(12) United States Patent
Aoyama et al.

(10) Patent No.: US 7,721,872 B2
(45) Date of Patent: May 25, 2010

(54) TRANSFER APPARATUS

(75) Inventors: Hiroshi Aoyama, Akashi (JP); Ryoichi Nishigawa, Akashi (JP)

(73) Assignee: Hallys Corporation, Akashi-shi (JP)

( * ) Notice: Subject to any disclaimer, the term of this patent is extended or adjusted under 35 U.S.C. 154(b) by 176 days.

(21) Appl. No.: 11/575,738

(22) PCT Filed: Sep. 21, 2005

(86) PCT No.: PCT/JP2005/017422

§ 371 (c)(1),
(2), (4) Date: Mar. 21, 2007

(87) PCT Pub. No.: WO2006/033370

PCT Pub. Date: Mar. 30, 2006

(65) Prior Publication Data

US 2008/0023296 A1 Jan. 31, 2008

(30) Foreign Application Priority Data

Sep. 22, 2004 (JP) ............................ 2004-275061

(51) Int. Cl.
*B65G 29/00* (2006.01)
(52) U.S. Cl. ................... 198/474.1; 198/476.1
(58) Field of Classification Search .............. 198/418.3, 198/471.1, 474.1, 476.1, 477.1, 482.1
See application file for complete search history.

(56) References Cited

U.S. PATENT DOCUMENTS

| | | | |
|---|---|---|---|
| 2,860,760 A * | 11/1958 | Yeo et al. ................... | 198/468.4 |
| 3,946,931 A | 3/1976 | Bahnck et al. | |
| 3,986,920 A | 10/1976 | Wearing et al. | |
| 4,080,053 A | 3/1978 | Friday | |
| 4,372,802 A | 2/1983 | Harigane et al. | |
| 4,506,779 A * | 3/1985 | Seragnoli ................. | 198/459.1 |
| 4,548,668 A | 10/1985 | Roth et al. | |
| 4,619,043 A | 10/1986 | Takahashi et al. | |
| 4,880,102 A | 11/1989 | Indrebo | |
| 4,893,982 A | 1/1990 | Yamaguchi | |
| 4,915,565 A | 4/1990 | Bond et al. | |
| 4,951,388 A | 8/1990 | Eguchi et al. | |
| 5,000,806 A | 3/1991 | Merkatoris et al. | |
| 5,025,910 A | 6/1991 | Lasure et al. | |

(Continued)

FOREIGN PATENT DOCUMENTS

EP    0 534 454 B1    12/1993

(Continued)

*Primary Examiner*—James R Bidwell
(74) *Attorney, Agent, or Firm*—Westerman, Hattori, Daniels & Adrian, LLP

(57) ABSTRACT

A transfer apparatus has a first conveying device for holding and conveying a transferring-work to be transferred; a second conveying device for holding and conveying a carrier work on which the transferring-work is placed; and a transfer device to receive the transferring-work from the first conveying device and transfer the transferring-work to the carrier work of the second conveying device. The transfer device has two or more end-effectors that revolve along the same circumference to convey the transferring-work, and each of the end-effectors revolves independently of the other end-effectors. Each of the end-effectors has a holding surface that holds the transferring-work, and the holding surface is able to advance and retract along a revolution axis of each of the end-effectors.

17 Claims, 16 Drawing Sheets

U.S. PATENT DOCUMENTS

| | | |
|---|---|---|
| 5,045,148 A | 9/1991 | Hoffstetter et al. |
| 5,150,164 A | 9/1992 | Shea |
| 5,222,854 A | 6/1993 | Blatt et al. |
| 5,268,724 A | 12/1993 | Koizumi et al. |
| 5,275,685 A | 1/1994 | Stauber |
| 5,389,173 A | 2/1995 | Merkatoris et al. |
| 5,507,909 A | 4/1996 | Rollins et al. |
| 5,749,455 A | 5/1998 | Mizuta et al. |
| 5,882,474 A | 3/1999 | Gomes et al. |
| 6,115,213 A | 9/2000 | Ikeda et al. |
| 6,314,786 B1 | 11/2001 | Hofele et al. |
| 6,471,802 B1 | 10/2002 | Williamson |
| 6,520,318 B1 * | 2/2003 | Humele .................. 198/483.1 |
| 6,598,647 B1 | 7/2003 | Draghetti |
| 6,604,623 B2 | 8/2003 | Sumi et al. |
| 6,656,312 B1 | 12/2003 | Schmitz et al. |
| 6,672,448 B2 | 1/2004 | Arai et al. |
| 6,722,494 B2 | 4/2004 | Nakakado |
| 6,748,996 B2 | 6/2004 | Nakakado et al. |
| 6,883,576 B1 | 4/2005 | Rello et al. |
| 6,913,664 B2 | 7/2005 | Umebayashi et al. |
| 7,097,725 B2 | 8/2006 | Yoneoka et al. |
| 7,192,502 B2 | 3/2007 | Spatafora et al. |
| 7,195,684 B2 | 3/2007 | Satoh |
| 2001/0047582 A1 | 12/2001 | Gallagher |
| 2002/0125105 A1 | 9/2002 | Nakakado |
| 2004/0177669 A1 | 9/2004 | Suzuki et al. |

FOREIGN PATENT DOCUMENTS

| | | |
|---|---|---|
| EP | 0 749 270 B1 | 12/1996 |
| EP | 1 162 162 A1 | 12/2001 |
| JP | H01-319999 A | 12/1989 |
| JP | H10-145091 A | 5/1998 |
| JP | 2002-214289 A | 7/2002 |
| JP | 2003-137420 A | 5/2003 |
| WO | 01/44086 A1 | 6/2001 |

* cited by examiner

TRANSFER APPARATUS

CROSS-REFERENCE TO RELATED APPLICATIONS

The benefit of priority is claimed to International Application PCT/JP2005/017422, filed Sep. 21, 2005, and published as WO 2006/033370 on Mar. 30, 2006; and the benefit of priority is also claimed to Japanese Patent Application No. 2004-275061, filed Sep. 22, 2004, with the Japan Patent Office, the disclosures of which are incorporated herein by reference in their entireties. In addition, U.S. Pre-grant Publication 2004/0154161, published Aug. 12, 2004, and International Publication WO 2006/033369, published Mar. 30, 2006, are also incorporated herein by reference in their entireties.

TECHNICAL FIELD

The present invention relates to a transfer apparatus that transfers a transferring-work to a carrier work, inter alia.

BACKGROUND

There has been known a transfer apparatus that transfers small pieces of transferring-works to predetermined positions on a surface of a carrier work, as a device for mounting electronic components. An example of the transfer apparatus includes a transfer head that revolves while holding a transferring-work. In such a transfer apparatus, for example, a cam is used to temporarily stop revolution of the transfer head, thereby allowing the transferring-work to be received or transferred to a carrier work with high accuracy.

The conventional transfer apparatus, however, has a problem in that temporary stops of revolution of the transfer head may prevent a sufficient increase in transfer efficiency.

One example of a conventional transfer apparatus is set forth in Japanese Patent Laid-Open No. H10-145091, the contents of which are incorporated herein by reference in its entirety.

The present invention is achieved in view of the problem of the conventional transfer apparatus, and has an object to provide a transfer apparatus with high transfer efficiency.

SUMMARY

The transfer apparatus in accordance with a first example comprises: a first conveying device for holding and conveying a transferring-work; a second conveying device for holding and conveying a carrier work; and a transfer device for receiving the transferring-work from the first conveying device and transferring the transferring-work to the carrier work, in which the transfer device comprises two or more end-effectors that revolve along the same circumference to convey the transferring-work, each of the end-effectors is configured to revolve independently of at least any of the other end-effectors, each of the end-effectors has a holding surface for holding the transferring-work, and is able to advance and retract the holding surface along a revolution axis of the each end-effector.

In the transfer apparatus of the first example, each end-effector can revolve independently of at least any of the other end-effectors. Thus, each end-effector can efficiently receive the transferring-work in response to changes in conveying speed or conveying position, etc., of the transferring-work conveyed by the first conveying device. Each end-effector can transfer the transferring-work with high accuracy in response to a conveying speed of the carrier work conveyed by the second conveying device, or a target transfer position or the like. Thus, the transfer apparatus can maintain high positional accuracy in receipt or transfer of the transferring-work without stopping the end-effectors.

Further, each end-effector of the first example is able to advance and retract the holding surface that holds the transferring-work along the revolution axis. Thus, the transfer apparatus can advance and retract the holding surface according to the position of the transferring-work conveyed by the first conveying device or displacement of the carrier work in the second conveying device, or the like. Therefore, the transfer apparatus can transfer the transferring-work with higher positional accuracy.

As described above, the transfer apparatus can efficiently transfer the transferring-work without temporarily stopping the end-effectors. Further, each end-effector can advance and retract the holding surface along the revolution axis, thereby allowing the transferring-work to be transferred with high positional accuracy.

The second example provides a transfer apparatus comprising: a first conveying device for holding and conveying a transferring-work; a second conveying device for holding and conveying a carrier work; and a transfer device for receiving the transferring-work from the first conveying device and transferring the transferring-work to the carrier work, in which the transfer device comprises two or more end-effectors that revolve along the same circumference to convey the transferring-work, each of the end-effectors is able to revolve independently of at least any of the other end-effectors, each of the end-effectors has a holding surface for holding the transferring-work, and the holding surface is rotatable around a central axis in the direction normal thereto.

In the transfer apparatus of the second example, each end-effector can revolve independently of at least any of the other end-effectors as in the first example. Thus, the transfer apparatus can maintain high positional accuracy in receipt or transfer of the transferring-work without stopping the end-effectors, as in the first invention.

Further, for each end-effector of the second example, the holding surface is rotatable around the central axis in the direction normal thereto. Thus, the transfer apparatus can rotate the holding surface as appropriate in response to an attitude of the transferring-work conveyed by the first conveying device, or an attitude of the carrier work in the second conveying device. Therefore, the transfer apparatus can transfer the transferring-work with higher positional accuracy.

As described above, the transfer apparatus can efficiently transfer the transferring-work without temporarily stopping each end-effector. Further, each end-effector can rotate the holding surface, thereby allowing the transferring-work to be transferred with extremely high accuracy.

DETAILED DESCRIPTION

Figure 1:
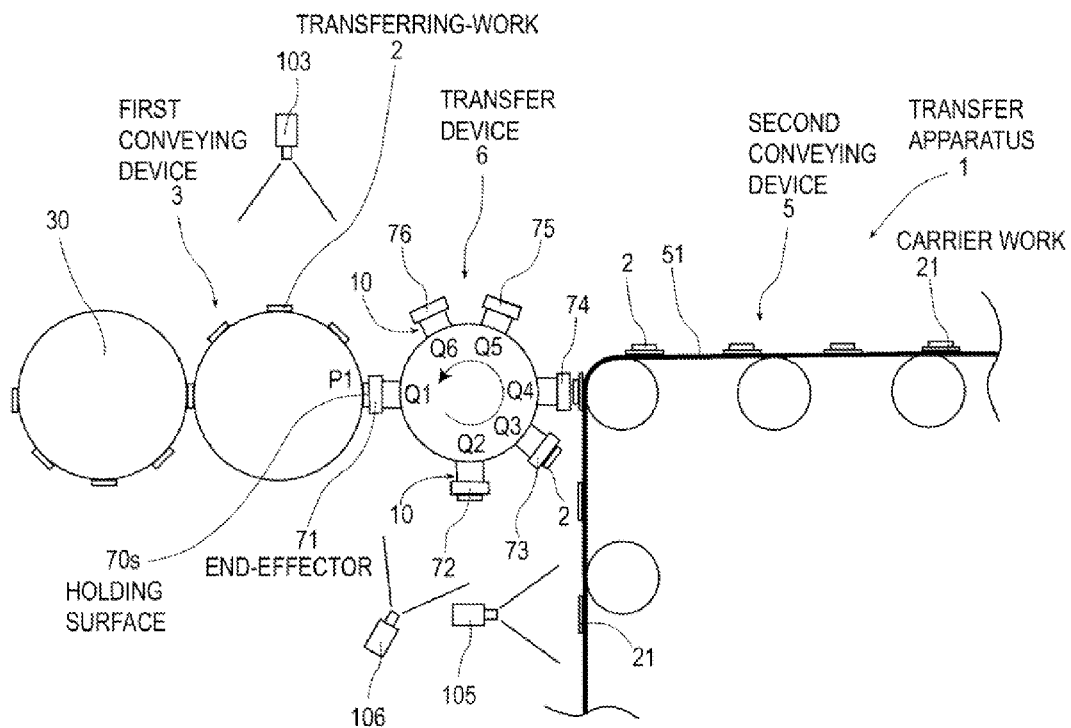
FIG. 1 is a block diagram of a transfer apparatus in Embodiment 1.

In the transfer apparatus of the first and the second embodiments, each end-effector can revolve independently of at least any of the other end-effectors. This allows the transferring-work to be received and transferred with high flexibility and efficiency as compared with, for example, the case where all the end-effectors integrally revolve. Particularly, speed control of the end-effector during revolution in the transfer apparatus allows revolution position control of the end-effector, and allows adjustment of timing for the each end-effector to receive the transferring-work. This can accommodate variations in position of the transferring-work conveyed by the first conveying device in a conveying direction, and allows the transferring-work to be transferred to the carrier work with high positional accuracy. Particularly, when all the end-effectors can revolve independently of one another, the operation and effect of the present invention can be further improved.

Similarly, revolution position control of each end-effector during revolution allows adjustment of timing for the transferring-work to be transferred to the carrier work. This can increase transfer accuracy of the transferring-work to the carrier work.

As described above, with the transfer apparatus of the first and the second embodiments, the operation of the transfer device provided between the first conveying device and the second conveying device can accommodate variations in position of the transferring-work in the conveying direction in the first conveying device, and allows the transferring-work to be transferred to the carrier work with high accuracy and efficiency.

Further, the transfer apparatus of the first and the second embodiments includes the plurality of end-effectors that revolve along the same circumference. With the plurality of end-effectors, the transferring-work can be transferred with extremely high efficiency while reducing the revolution speed of the end-effectors. For example, with six end-effectors each controlled so as to revolve independently, the transferring-work can be transferred at a high speed cycle of one sixth of a revolution cycle of an end-effector.

The transfer apparatus of the first and the second embodiments can be used for production processes of, for example, RF-TAGs, disposable diapers, sanitary napkins, or tampons. For example, in the production process of RF-TAGs, the transfer apparatus can be used in a step of transferring interposers to an antenna sheet. Further, for example, in the production processes of disposable diapers or sanitary napkins, or the like, the transfer apparatus can be used in a step of transferring adhesive tapes or water-absorbing pads to a resin film such as a polyethylene film or nonwoven fabric.

In the first embodiment, the holding surface is preferably rotatable around a central axis in the direction normal thereto. In this case, the holding surface can be rotated as appropriate according to the attitude of the transferring-work conveyed by the first conveying device or the attitude of the carrier work in the second conveying device. Thus, the transfer apparatus can transfer the transferring-work with higher positional accuracy.

In the first and the second embodiments, it is preferable that the transfer apparatus comprises a controller for controlling a revolution speed and a revolution position in revolution of each end-effector, in which the controller can perform control so that the revolution speed of the end-effector when receiving the work from the first conveying device substantially matches a conveying speed of the first conveying device, and a revolution speed of the end-effector when transferring the work to the second conveying device substantially matches a conveying speed of the second conveying device.

In this case, the end-effectors that revolve along the same circumference synchronize with a conveying motion of the first conveying device while maintaining the sequential order of revolution thereof, and can receive the transferring-work from the first conveying device at a relative speed of substantially zero. Then, the end-effectors synchronize with a conveying motion of the second conveying device, and can transfer the transferring-work to the second conveying device at a relative speed of substantially zero.

In the transfer apparatus, the relative speed between the first conveying device and the end-effector is substantially zero when the end-effector receives the transferring-work from the first conveying device. Also, the relative speed between the second conveying device and the end-effector is substantially zero when the end-effector transfers the transferring-work to the second conveying device. Thus, the transfer device can continuously receive the transferring-works continuously conveyed, and then continuously transfer the received transferring-works to the second conveying device without stopping revolution of the end-effectors.

In the transfer apparatus, the relative speed between each of the conveying device and the end-effector is substantially zero in receipt or transfer of the work. Thus, the transfer apparatus can transfer the transferring-work with extremely high accuracy and extremely low possibility of damaging the transferring-work during conveyance.

Particularly, the operation and effect of the present invention is more effective when a difference in conveying speed exists between the first conveying device and the second conveying device. In this case, the end-effectors during revolution are variably controlled in their speed as needed to respond to respective conveying speeds with high accuracy. If the relative speed between the end-effector and the conveying device is substantially zero in receipt and transfer of the transferring-work, high conveying position accuracy of the transferring-work can be maintained.

It is preferable that the transfer device includes coaxial rotors that integrally hold one or more end-effectors revolving therewith, and three or more bearings placed coaxially so as to rotatably support at least two coaxial rotors, each of the bearings includes a substantially cylindrical inner ring, a substantially cylindrical outer ring fitted from outside to the inner ring, and a bearing mechanism that allows relative rotation between the inner ring and the outer ring, the inner ring of one or more middle bearings placed in an axially middle position among the bearings is connected to the outer ring of adjacent another bearing and integrally rotates therewith, and integrally holds any of the coaxial rotors, the inner ring of one of the bearings placed at axial ends among the bearings is connected to the outer ring of an adjacent bearing and integrally rotates therewith, and integrally holds any of the coaxial rotors, and the outer ring thereof is secured to a structure member of the transfer device, the outer ring of the other of the bearings placed at the axial ends among the bearings is connected to the inner ring of an adjacent bearing and integrally rotates therewith, and the inner ring thereof is secured to a structure member of the transfer device, and the outer rings integrally connected to the inner rings of the adjacent bearings among the outer rings are connected to an output shaft of an external motor whose rotation is independently controlled.

In this case, the inner ring of one of the adjacent bearings and the outer ring of the other of the bearings are connected to achieve an integral bearing structure including the plurality of bearings. Specifically, a structure can be achieved in which the coaxial rotors each support the other coaxial rotors.

Further, with such a support structure, a rotation driving force supplied from the external motor to the outer ring can rotatably drive the coaxial rotor integrally held by the inner ring and revolvably drive the end-effector integrally held by the coaxial rotor. In case three coaxial rotors are included, application of the rotation driving force from three directions allows an external pressure (stress) toward an axis acting on each bearing to be averaged and reduced.

As the external motor, a servo-controlled motor may be used, and a direct drive mechanism that can achieve control with high accuracy may be used. The output shaft of the external motor and the outer ring can be directly connected, or indirectly connected via a gear or a timing belt.

The transfer apparatus preferably comprises a first measuring portion to detect a conveying position and a conveying speed of the transferring-work conveyed by the first conveying device.

In this case, revolution of the end-effector can be controlled based on the conveying position and the conveying speed of the transferring-work in the first conveying device. For example, as compared with the case where the end-effector is controlled using indirect information such as control information of the first conveying device, or the like, the transferring-work can be received at higher speed with higher accuracy.

The transfer apparatus preferably comprises a second measuring portion to detect a target transfer position on a surface of the carrier work in the second conveying device and a movement speed thereof.

In this case, revolution of the end-effector can be controlled based on the target transfer position on the surface of the carrier work or the movement speed thereof. For example, as compared with the case where the end-effector is controlled using indirect information such as control information of the second conveying device, or the like, the transferring-work can be transferred at higher speed with higher accuracy.

The transfer apparatus preferably comprises a third measuring portion to detect an attitude and a position of the transferring-work held by the holding surface of the end-effector.

In this case, the attitude and the position of the transferring-work on the holding surface can be detected using the third measuring portion. The attitude or the position of the transferring-work can be adjusted based on the detection results to prevent displacement of the transferring-work. This allows the transferring-work to be transferred to the carrier work with higher positional accuracy.

It is preferable that the first and the second conveying devices each include a roller or a translating conveyor belt, and can convey the transferring-work or the carrier work placed on a surface of the roller or the conveyer belt.

In this case, the transfer apparatus with high conveying efficiency can be configured using the roller or the conveyor belt.

It is preferable that the transferring-work is an interposer on which IC chips for RF-TAGs are mounted and an enlarged electrode electrically extended from electrodes of the IC chips is formed, and the carrier work is an antenna sheet having an antenna pattern for radio communication formed on a sheet substrate.

In this case, electronic components that constitute accurate RF-TAGs can be efficiently produced using the transfer apparatus of the first or second embodiment.

Embodiment 1

This embodiment relates to a transfer apparatus 1 that transfers a transferring-work 2 to a carrier work 21. This will be described with reference to FIGS. 1 to 11.

As shown in FIG. 1, the transfer apparatus 1 of the first embodiment includes a first conveying device 3 for holding and conveying the transferring-work 2, a second conveying device 5 for holding and conveying the carrier work 21, and a transfer device 6 for receiving the transferring-work 2 from the first conveying device 3 and transferring the transferring-work 2 to the carrier work 21 in the second conveying device 5.

The transfer device 6 includes two or more end-effectors 71 to 76 that revolve along the same circumference and convey the transferring-works 2, and each of the end-effectors 71 to 76 can revolve independently of at least any of the other end-effectors.

Each of the end-effectors 71 to 76 has a holding surface 70s that holds the transferring-work 2, and can advance and retract the holding surface 70s along a revolution axis CL (see FIG. 4) of each of the end-effectors 71 to 76. Now, this will be described in more detail.

Figure 2:
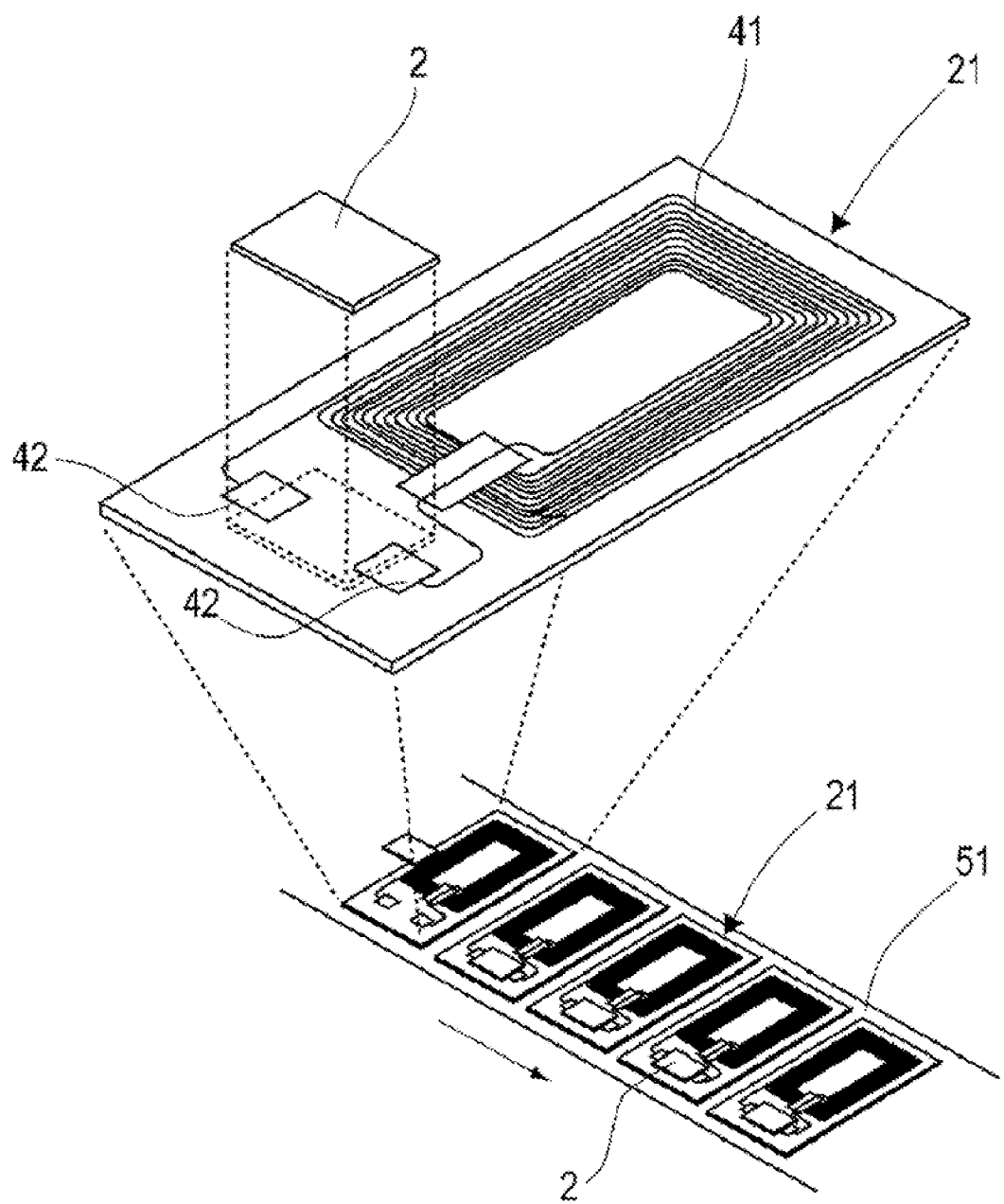
FIG. 2 illustrates an arrangement of a transferring-work on a carrier work in Embodiment 1.

The transfer apparatus 1 of the first embodiment is intended to produce RF-TAGs. As shown in FIG. 2, the transfer apparatus 1 can perform a transfer process with an RF-TAG component formed with an antenna 41 as the carrier work 21, and an electronic component for RF receiving and transmitting processing as the transferring-work 2.

The carrier work 21 includes the antenna 41 provided on a surface of a PET film. The transferring-work 2 is an interposer having an IC for RF receiving and transmitting processing mounted on the surface of a resin sheet, and having an enlarged electrode. The carrier work 21 includes a pair of terminals 42 extended from the antenna 41 and can mount the transferring-work 2 between the terminals 42. In the embodiment, the transferring-work 2 is placed on the carrier work 21 with accuracy of several hundred microns to several tens of microns.

As shown in FIG. 1, the first conveying device 3 is a substantially cylindrical roller, and holds the transferring-works 2 on an outer peripheral surface thereof. The first conveying device 3 receives the transferring-works 2 from an adjacent transferring-work supply device 30 and then transfer the transferring-works 2 to the transfer device 6. The transferring-work supply device 30 feeds a continuous tape holding the transferring-works 2 by a substantially cylindrical roller. Alternatively, the transferring-work supply device 30 may be configured as an individual separation and supply device that separates the transferring-works 2 from a continuous sheet material into individual pieces and supplies the pieces to the first conveying device 3.

As shown in FIG. 1, the first conveying device 3 can transfer the transferring-work 2 to the end-effector 71 at a point P1. The first conveying device 3 holds the transferring-works 2 on an outer surface at substantially regular intervals. A hole (not shown) communicating with a suction port of a pump is provided in a surface of the first conveying device 3 constituted by a roller. The first conveying device 3 sucks and holds the transferring-work 2 with the hole in the surface of the roller under negative pressure. On the other hand, the transferring-work 2 is released at the point P1 with the hole in the surface of the roller under positive pressure or atmospheric pressure. In this embodiment, the first conveying device 3 is controlled so as to operate at substantially constant speed by a drive source and a drive control system.

As shown in FIG. 1, the second conveying device 5 has a conveyor belt 51. The second conveying device 5 can hold and convey the carrier works 21 at substantially regular intervals on a surface of the conveyor belt 51. A hole (not shown) communicating with a suction port of an unshown pump is provided in a surface of the conveyor belt 51. The second conveying device 5 can suck and hold the carrier works 21 with the hole in the surface of the conveyor belt 51 under negative pressure. In the first embodiment, the second conveying device 5 is controlled so as to operate at substantially constant speed by a drive source and a drive control system.

In the embodiment, the individual carrier works 21 are held and conveyed by the conveyor belt 51. Alternatively, individual carrier works 21 may be held by a belt-like holder, or transferring-works 2 may be mounted on a continuous tape-like flexible substrate on which antennas 41 are continuously provided by printing or photography and then cut into individual pieces.

The transfer apparatus 1 in the first embodiment includes an imaging device (a measuring portion) 103 for photographing a conveying state of the transferring-work 2 under conveyance by the first conveying device 3 and obtaining image data. In the first embodiment, the image data is subjected to image processing to detect a conveying position and a conveying speed of the transferring-work 2 under conveyance. A control device controls revolution of the end-effectors 71 to 76 based on the detected conveying position and conveying speed.

Further, as shown in FIG. 1, the transfer apparatus 1 in the embodiment includes an imaging device (a measuring portion) 106 for photographing a state of the transferring-works 2 held by the end-effectors 71 to 76, and an imaging device (a measuring portion) 105 for photographing a conveying state of the transferring-works 2 in the second conveying device 5. Based on image data obtained by photographing with the imaging devices 105 and 106, for example, abnormalities of the transferring-work 2 or the carrier work 21 can be detected such as an abnormal conveying interval, an abnormal attitude, or foreign matter.

Particularly, in the first embodiment, an advancing and retracting mechanism and a rotating mechanism described later are controlled based on the image data obtained by the imaging devices 103, 105 and 106. The imaging devices 103, 105 and 106 may include CCDs or CMOS devices, or inexpensive optical sensors.

Figure 3:
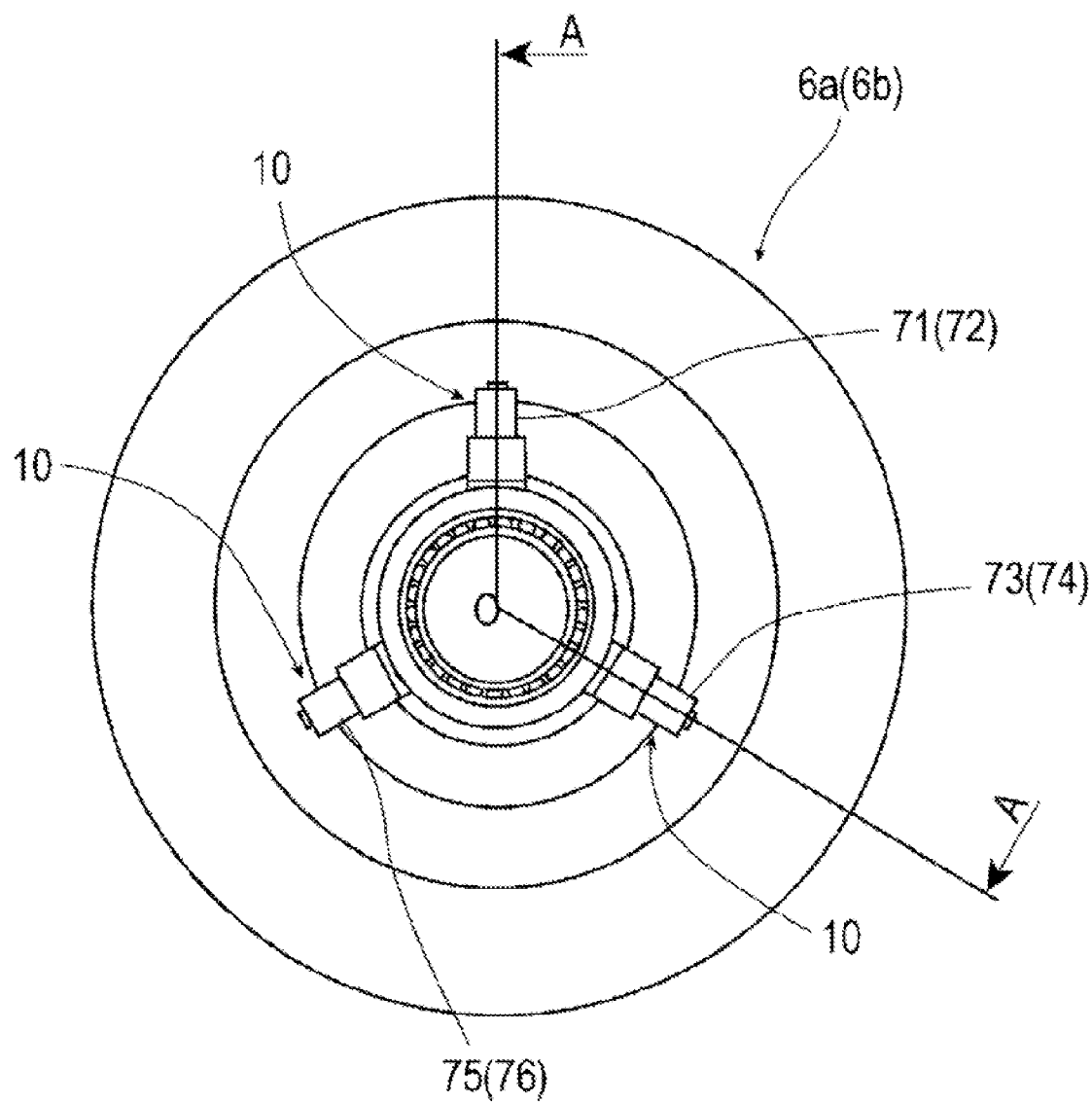
FIG. 3 is a front view of a transfer device in Embodiment 1.
Figure 4:
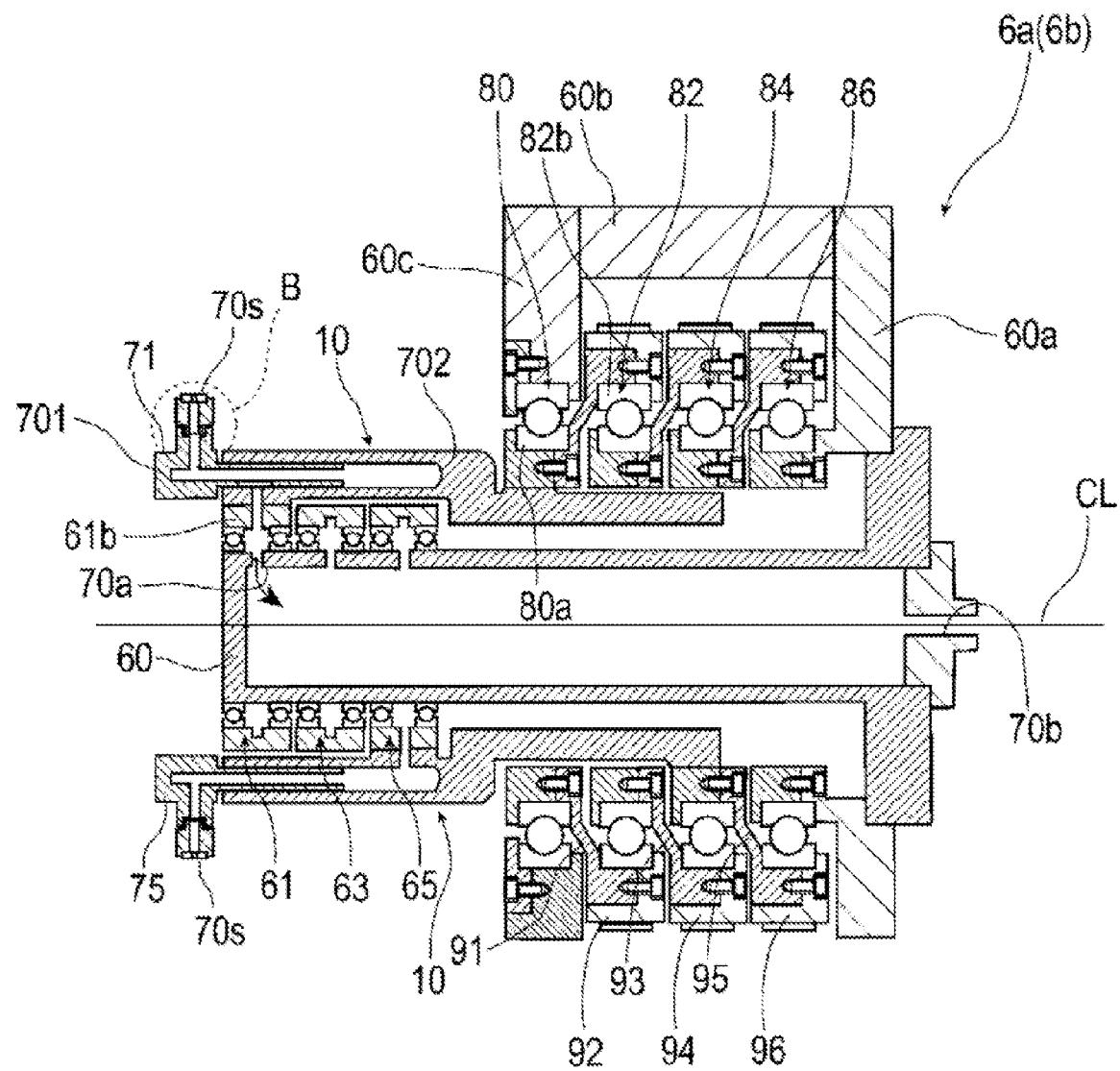
FIG. 4 is a sectional view of a sectional structure of the transfer device in Embodiment 1, viewed along arrows A-A in FIG. 2.
Figure 5:
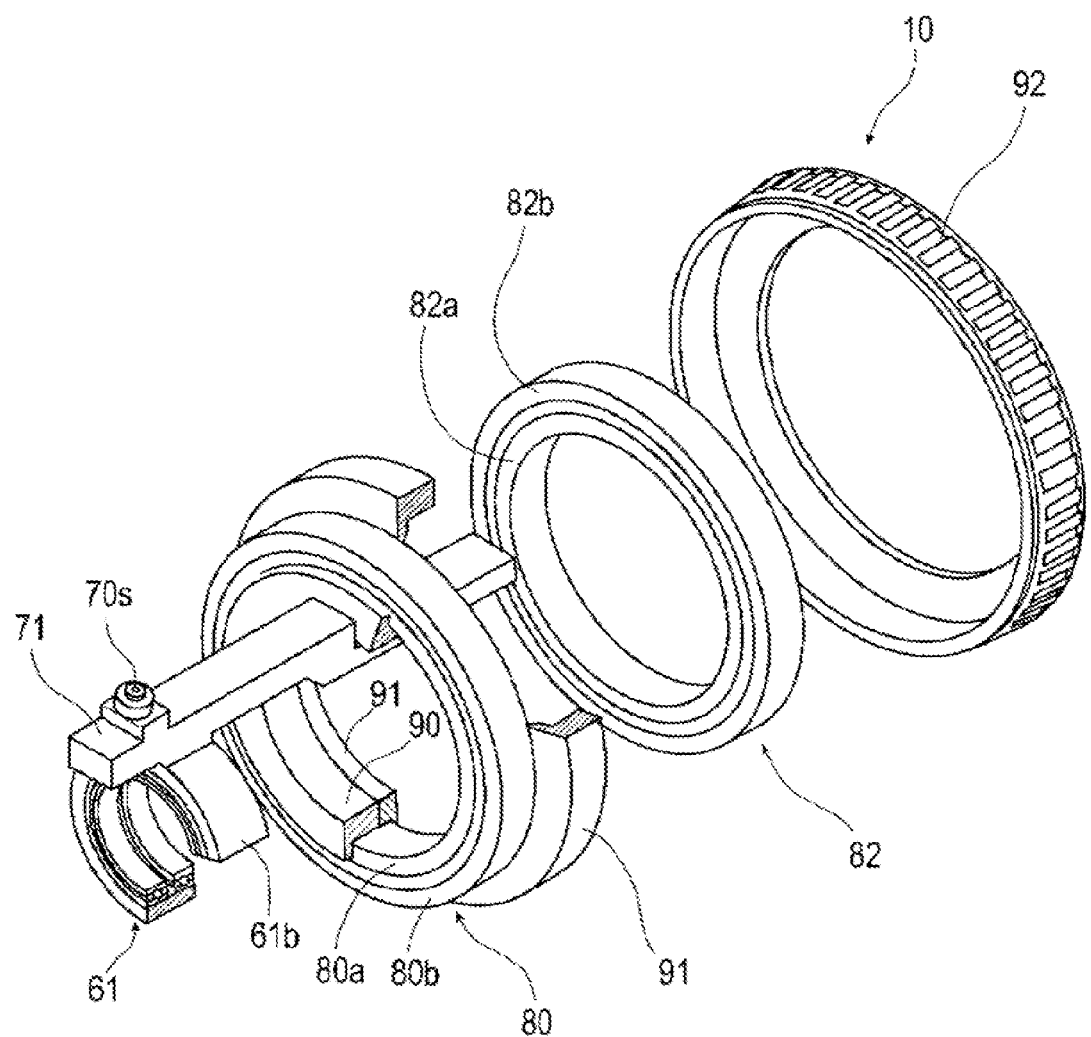
FIG. 5 is a perspective view of an assembling structure of a coaxial rotor in Embodiment 1.

The transfer device 6 is constituted by a combination of two transfer devices 6a and 6b having the same specifications. As shown in FIGS. 3 to 5, each transfer device 6a, 6b is constituted by a combination of three coaxial rotors 10. As shown in FIGS. 3 and 4, the transfer device 6a, 6b includes structure members 60a, 60b and 60c, and four bearings 80, 82, 84 and 86 coaxially placed. A hollow shaft 60 as a structure member is provided on an inner peripheral side of the bearings 80, 82, 84 and 86. On an outer periphery of the hollow shaft 60, bearings 61, 63 and 65 for supporting revolution of the coaxial rotors 10 are placed.

The transfer device 6a, 6b has a structure in which the coaxial rotors 10 support one another. Specifically, an inner ring of one of axially adjacent bearings and an outer ring of the other bearing are integrally connected via connecting members 91, 93 and 95. Among the combination of the inner ring and the outer ring connected via the connecting member 91, 93 or 95, the coaxial rotor 10 is integrally secured to an inner peripheral side of the inner ring, and a drive wheel 92, 94 or 96 is fitted over the outer ring and secured.

In the transfer device 6a, 6b in the embodiment thus configured, a rotation driving force is supplied to the three drive wheels 92, 94 and 96 from three directions at circumferentially equally spaced intervals around the revolution axis CL. This cancels external pressure of the drive wheels 92, 94 and 96 of the coaxial rotors 10 toward the axis. In the transfer device 6a, 6b, general purpose servo-controlled motors (external motors) are connected independently to the drive wheels 92, 94 and 96. This allows independent control of revolution of the coaxial rotors 10 (the end-effectors 71, 73 and 75 and/or 72, 74 and 76).

As shown in FIG. 5, each coaxial rotor 10 has one end-effector. As shown in FIGS. 3 and 4, the end-effectors 71, 73 and 75 (72, 74 and 76) are rod members offset placed substantially in parallel with the revolution axis CL. The end-effector 71, 73, 75 (72, 74, 76) are supported revolvably around the revolution axis CL.

In the transfer device 6a, 6b of the embodiment, open space is provided on the outer peripheral side of the drive wheels 92, 94 and 96 in the structure thereof. Thus, various mechanisms can be provided on the outer peripheral side of the drive wheels 92, 94 and 96. For example, a direct drive mechanism that allows more accurate control may be provided instead of the general purpose servo-controlled motor. In the embodiment, conductive meshing grooves (precision gears or the like) are provided in the outer peripheral surfaces of the drive wheels 92, 94 and 96 so that the drive wheels 92, 94 and 96 can be rotatably driven by a timing belt.

Figure 8A:
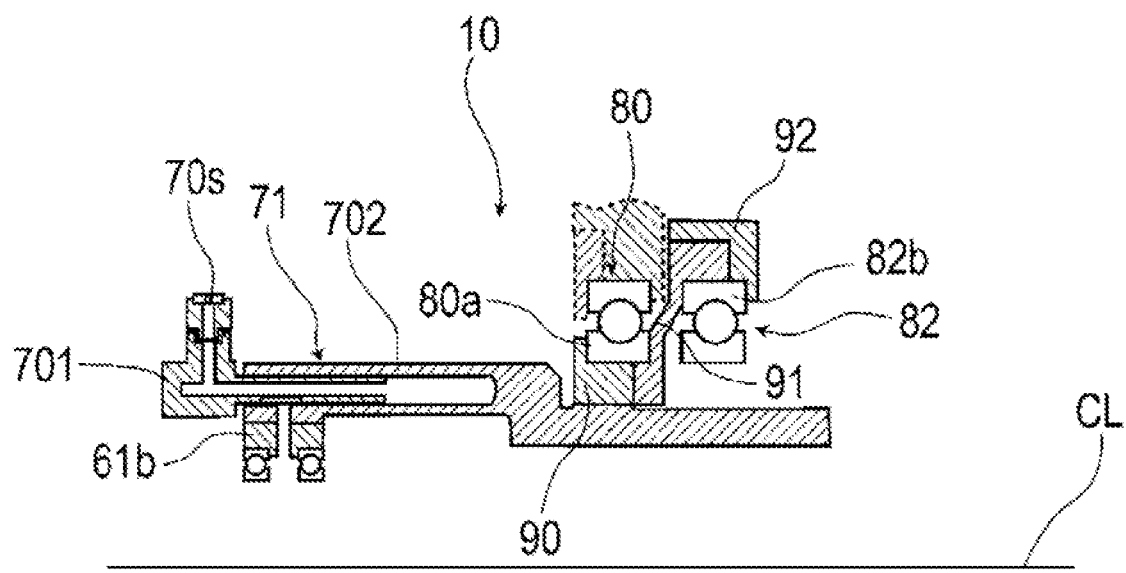
FIG. 8A is a sectional view showing one coaxial rotor individually in Embodiment 1.
Figure 8B:
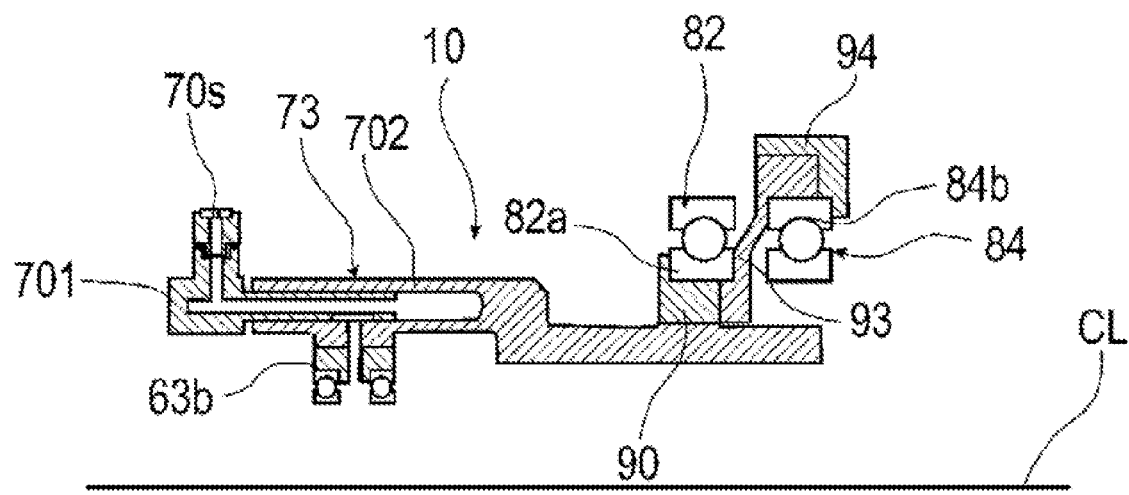
FIG. 8B is a sectional view showing one coaxial rotor individually in Embodiment 1.
Figure 8C:
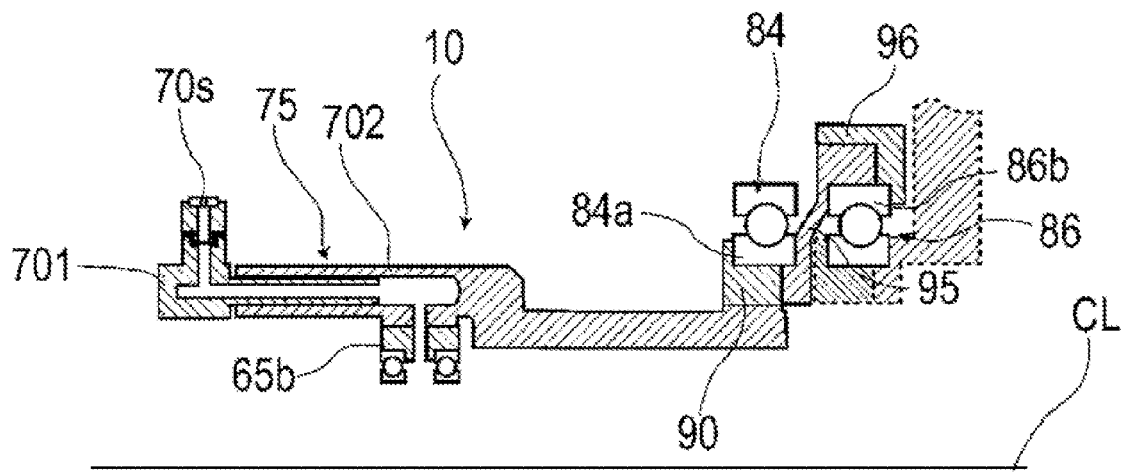
FIG. 8C is a sectional view showing one coaxial rotor individually in Embodiment 1.

As shown in FIGS. 5 and 8, the coaxial rotor 10 has one of the end-effectors 71 to 76. As shown in FIGS. 2 and 3, the end-effectors 71, 73 and 75 (72, 74 and 76) are rod members eccentrically placed substantially in parallel with the revolution axis CL. The end-effectors 71, 73 and 75 (72, 74 and 76) are supported revolvably around the revolution axis CL. As shown in FIG. 4, the end-effectors 71, 73 and 75 (72, 74 and 76) each have, at a tip thereof, a holding surface 70s for sucking and holding the transferring-work 2 (see FIG. 1). The holding surface 70s has a hole for controlling air pressure, and can suck and hold the transferring-work 2 under negative pressure. On the other hand, when the transferring-work 2 is transferred to the second conveying device 5, atmospheric pressure or positive pressure is formed in the hole in the holding surface 70s. A structure for achieving control of pressure in the hole in the holding surface 70s will be described later.

Further, as shown in FIG. 4, the end-effectors 71, 73 and 75 (72, 74 and 76) each include the rotating mechanism for rotating the holding surface 70s, and the advancing and retracting mechanism for advancing and retracting the holding surface 70s along the revolution axis CL.

As shown in FIG. 5, the end-effector 71 is secured on the tip side thereof (on the side of the holding surface 70s) to an outer periphery of an outer ring 61b of the bearing 61, and on the rear end side thereof to an inner periphery of an inner ring 80a of the bearing 80. The inner ring 80a of the bearing 80 is integrally connected to an outer ring 82b of the axially adjacent bearing 82 via the connecting member 91. The drive wheel 92 is secured on the outer peripheral side of the outer ring 82b via part of the connecting member 91.

As shown in FIG. 5, the end-effector 73 is secured on the tip side thereof (on the side of the holding surface 70s) to an outer periphery of an outer ring 63b of the bearing 63, and on the rear end side thereof to an inner periphery of an inner ring 82a of the bearing 82. The inner ring 82a of the bearing 82 is integrally connected to an outer ring 84b of the axially adjacent bearing 84 via the connecting member 93. The drive wheel 94 is secured on the outer peripheral side of the outer ring 84b via part of the connecting member 93.

As shown in FIG. 5, the end-effector 75 is secured on the tip side thereof (on the side of the holding surface 70s) to an outer periphery of an outer ring 65b of the bearing 65, and on the rear end side thereof to an inner periphery of an inner ring 84a of the bearing 84. The inner ring 84a of the bearing 84 is integrally connected to an outer ring 86b of the axially adjacent bearing 86 via the connecting member 95. The drive wheel 96 is secured on the outer peripheral side of the outer ring 86b via part of the connecting member 95.

Figure 7:
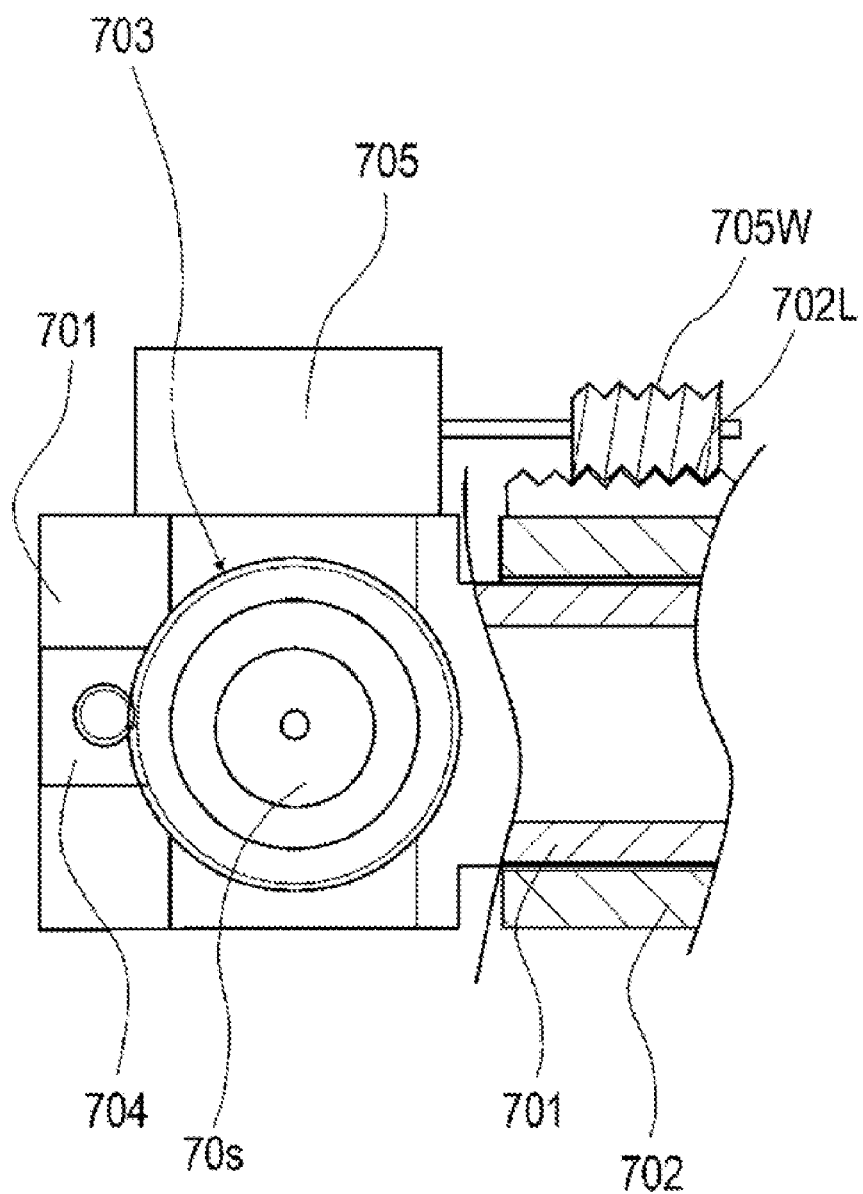
FIG. 7 is a front view of the holding surface in Embodiment 1, viewed along an arrow C in FIG. 6.

As shown in FIGS. 4 and 7, the advancing and retracting mechanism includes a support member 702 that constitutes a main body of each of the end-effectors 71 to 76, a sliding member 701 that supports the holding surface 70s on a holding base 703, and a motor 705 secured to the sliding member 701 (in FIG. 4, the motor 705 is omitted). The sliding member 701 is slidably inserted into a hollow portion in an inner periphery of the support member 702. A rack gear 702L is provided on an outer peripheral surface of the support member 702. A worm gear 705W fitting over an output shaft of the motor 705 engages the rack gear 702L so that rotation control of the motor 705 allows control of advance and retraction of the sliding member 701.

Figure 6:
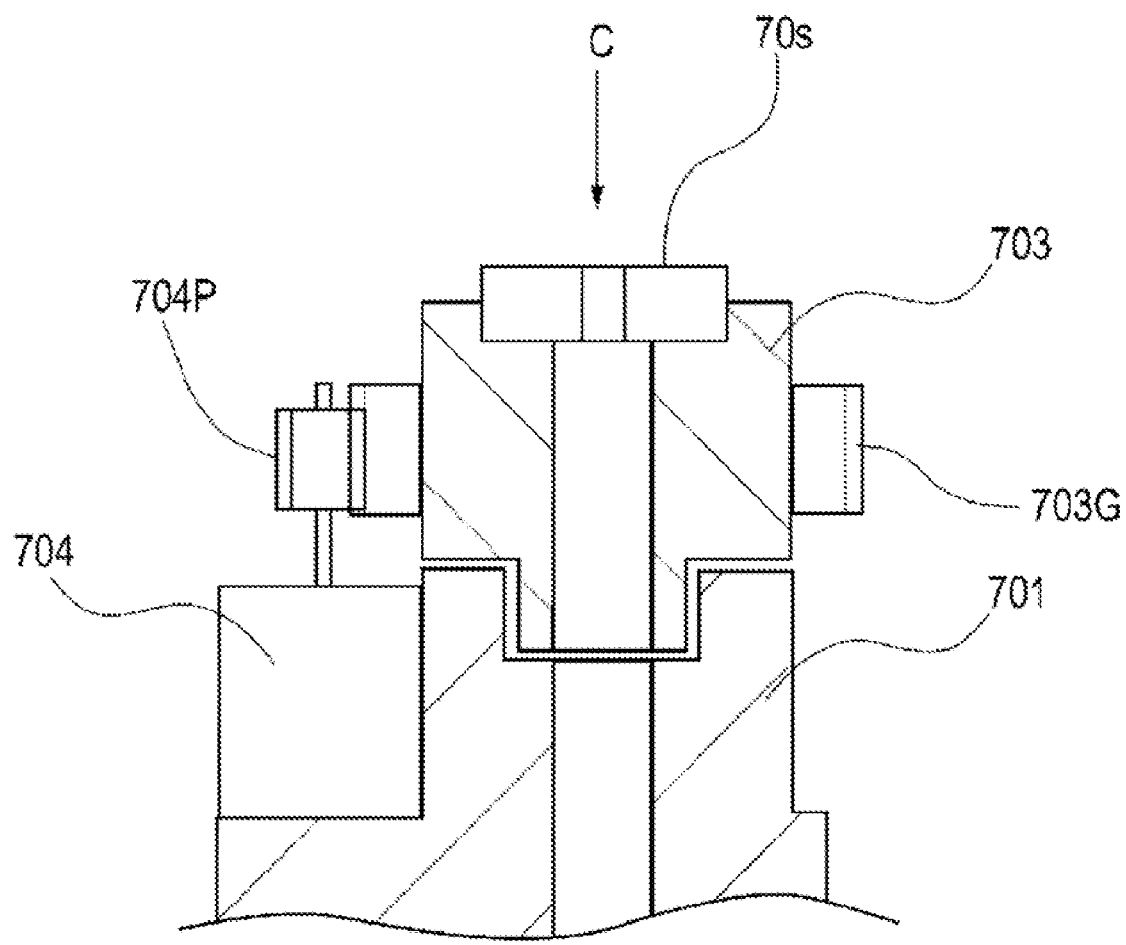
FIG. 6 is an enlarged sectional view of a peripheral structure of a holding surface in Embodiment 1 (an enlarged view of a part B in FIG. 4)

As shown in FIGS. 4, 6 and 7, the rotating mechanism includes the holding base 703 having the holding surface 70s and rotatably supported by the sliding member 701, and a motor 704 secured to the sliding member 701 (in FIG. 4, the motor 704 is omitted). The holding base 703 is a substantially disk-shaped member having a gear 703G on its outer peripheral surface. A gear 704P fitting over an output shaft of the motor 704 engages the gear 703G of the holding base 703. The rotating mechanism is configured so that rotation control of the motor 704 causes rotation of the holding base 703 and thus rotation of the holding surface 70s.

Figure 9:
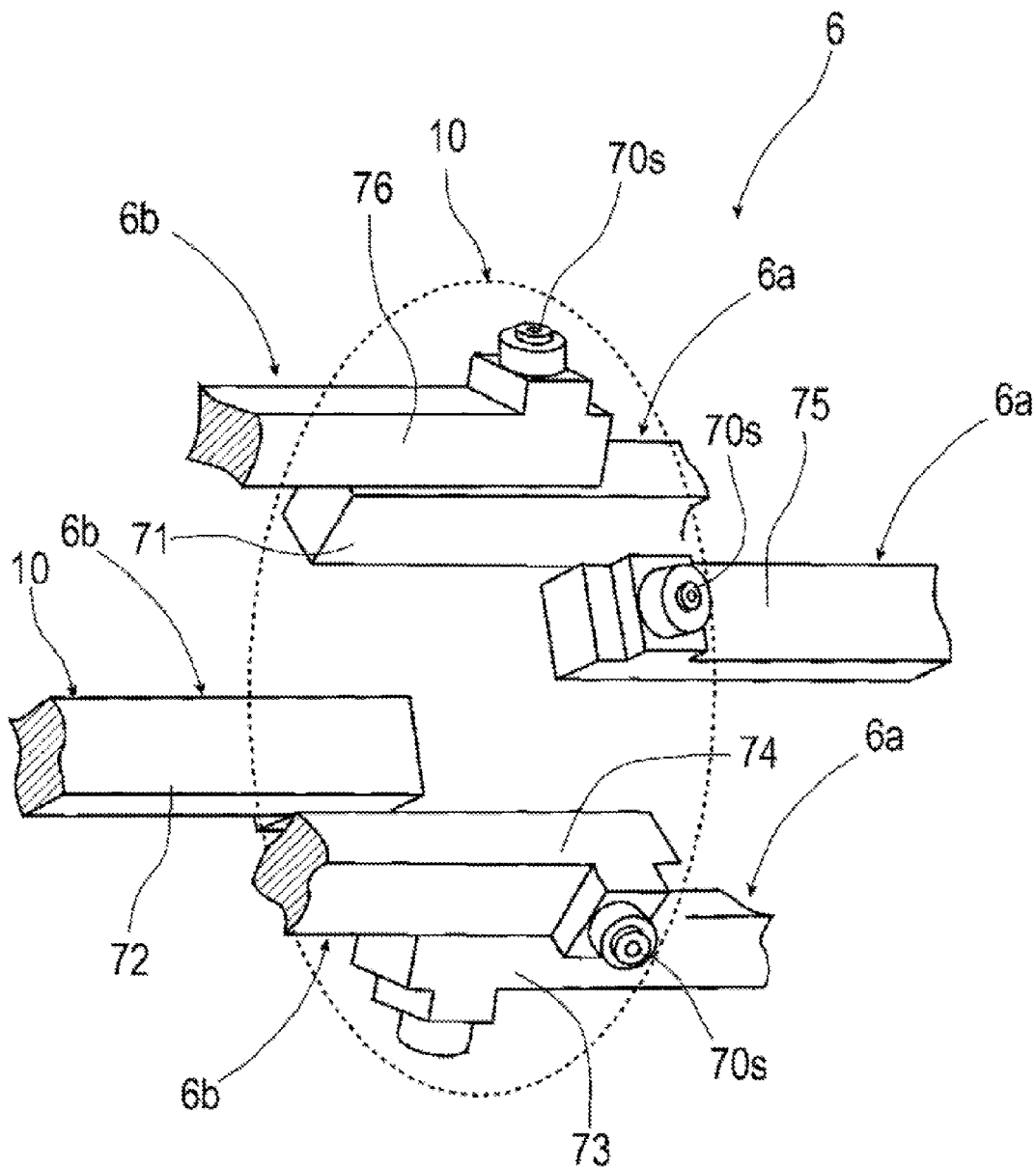
FIG. 9 illustrates end-effectors arranged on the same circumference in Embodiment 1.

As shown in FIG. 9, the transfer apparatus 1 in the embodiment is constituted by the combination of the two transfer devices 6a and 6b. The transfer device 6a includes the end-effectors 71, 73 and 75. The transfer device 6b includes the end-effectors 72, 74 and 76. As shown in the figure, the two transfer devices 6a and 6b are placed to face each other so that all the end-effectors 71 to 76 revolve along the same circumference.

In the transfer device 6 thus configured, the end-effectors 71 to 76 revolve along the same circumference. The end-effectors 71 to 76 synchronize with a conveying motion of the first conveying device 3 maintaining the sequential order of revolution thereof, and receive the transferring-works 2 from the first conveying device 3 at a relative speed of substantially zero. Then, the end-effectors 71 to 76 synchronize with a conveying motion of the second conveying device 5, and transfer the transferring-works 2 to the second conveying device 5 at a relative speed of substantially zero.

The end-effectors 71 to 76 revolve along the same circumference, and are independently subjected to cycle speed control during revolution including receipt and transfer. Specifically, on a revolution path of the end effectors, timing adjustment (revolution position adjustment) for receipt and transfer of the transferring-works 2 and the cycle speed control for adjusting the speed at that time are performed.

Next, a suction mechanism (a pressure control mechanism of the hole) in the holding surface 70s of the coaxial rotor in the embodiment will be described with reference to FIG. 1. For example, the transfer apparatus 1 in FIG. 1 is in the state where the end-effector 71 is receiving the transferring-work 2 from the first conveying device 3 (revolving position Q1), while the end-effectors 72 and 73 are moving toward the second conveying device 5 (revolving positions Q2 and Q3), and the end-effector 74 is transferring the transferring-work 2 to the second conveying device 5 (revolving position Q4). The end-effectors 75 and 76 are revolutionarily moving (revolving positions Q5 and Q6).

As shown in FIG. 4, a through hole 70b is provided along the revolution axis CL in an end surface of the hollow shaft 60 of the transfer device 6a, 6b. An intake port of a pump is connected to the through hole 70b. Thus, a hollow portion of the hollow shaft 60 is maintained under negative pressure by the action of the pump. A through hole 70a passing radially is provided in an outer peripheral wall surface of the hollow shaft 60. Further, holes passing radially and communicating with hollow portions of the end-effectors 71, 73 and 75 are provided in the bearings 61, 63 and 65 so as to communicate with the through hole 70a.

Particularly, the through hole 70a in the embodiment is provided in a predetermined circumferential position in the outer peripheral wall surface of the hollow shaft 60 so as to communicate with the end-effectors positioned in a revolution zone from the revolving position Q1 (strictly, a position short of the revolving position Q1 so that the holding surface 70s sucks the transferring-work 2 in the revolving position Q1) to the revolving position Q4 (strictly, a position short of the revolving position Q4 so that the holding surface 70s releases the transferring-work 2 in the revolving position Q4).

An atmospheric pressure introducing port (not shown in figures) is provided in a predetermined circumferential position in the outer peripheral wall surface of the hollow shaft 60 so as to introduce atmospheric pressure through the hole in the bearing 61 when the end-effector is positioned in the revolving position Q4. Thus, in the transfer device 6a in the embodiment, pressure control of the hole in the holding surface 70s is automatically performed in response to rotation of the bearings 61, 63 and 65 caused by the revolution of the end-effectors 71, 73 and 75.

Figure 10:
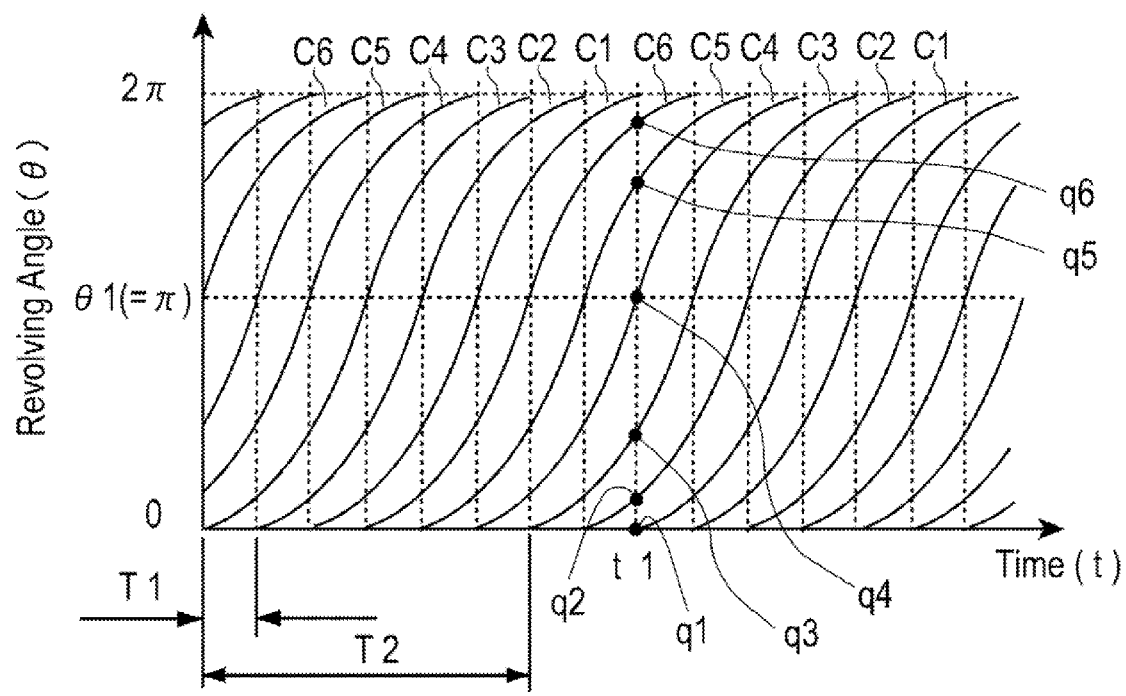
FIG. 10 is a graph illustrating revolution of the end-effectors in Embodiment 1.

Next, revolution of the end-effectors 71 to 76 will be described with reference to FIG. 10. FIG. 10 shows changes with time in revolving angles of the end-effectors 71 to 76. Curves C1 to C6 correspond to revolving movements of the end-effectors 71 to 76, respectively in FIG. 1. Points q1 to q6 at time t1 on the graph correspond to the revolving positions Q1 to Q6, respectively in FIG. 1. A contact position between the first conveying device 3 and the transfer device 6 (the revolving position Q1) in FIG. 1 is a home position of a revolving angle θ, and the revolving direction is counter-clockwise as shown in FIG. 1.

A cycle T1 in FIG. 10 is a cycle of the first conveying device 3 supplying the transferring-work 2 to the transfer device 6 (a work supply cycle). The work supply cycle is determined by the conveying speed of the first conveying device 3, and the interval between the transferring-works 2 on the conveyor belt 31. A cycle T2 is a cycle of revolution of each end-effector. A relationship of T2≈6×T1 is met in a short time period, and an average relationship in a long time period is T2=6×T1. In the embodiment, the six end-effectors 71 to 76 revolution-controlled independently are used. Thus, the transfer device 6 in the embodiment can accommodate a work supply speed about six times higher than a revolution speed of each end-effector.

Figure 11:
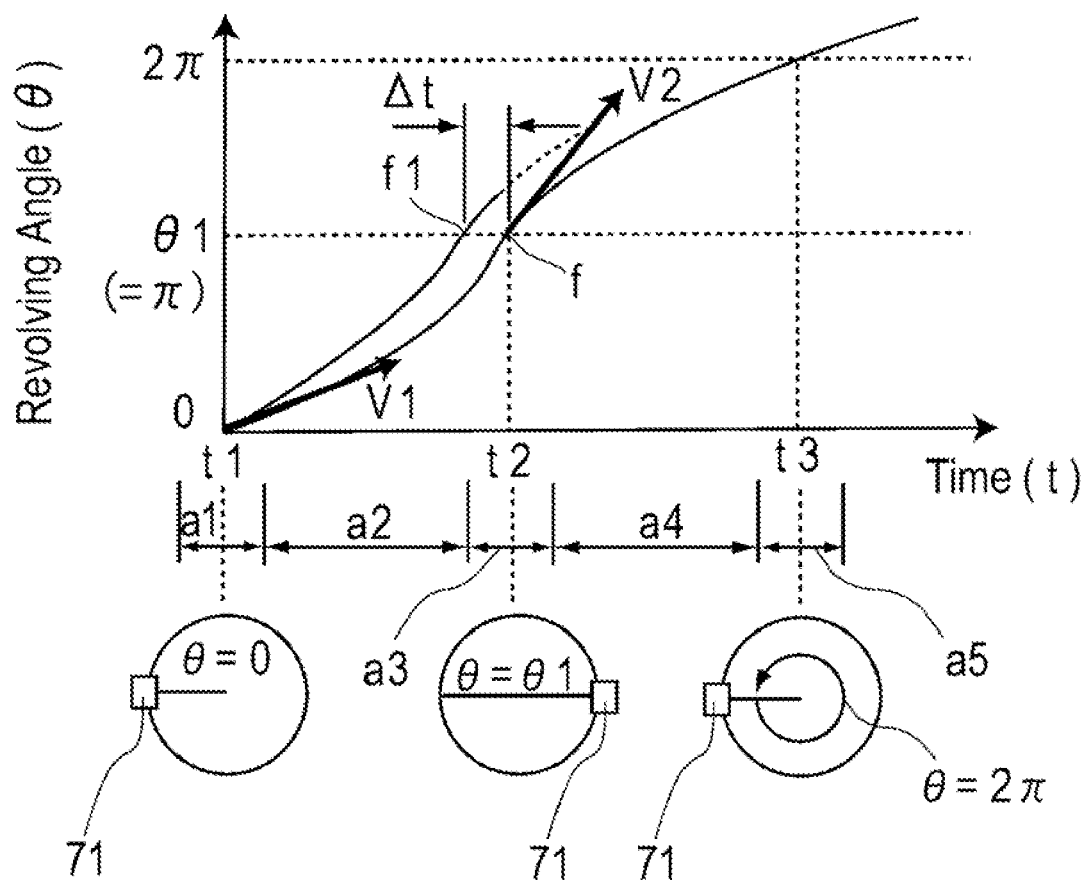
FIG. 11 is a graph illustrating revolution of one end-effector in Embodiment 1.

The revolution of the end-effector 71, by way of example, will be described. FIG. 11 shows changes with time in the revolving angle of the end-effector 71 during revolution. The end-effector 71 receives the transferring-work 2 from the first conveying device 3 at speed V1 at the time t=t1 with the revolving angle θ=0. Then, the end-effector 71 transfers the transferring-work 2 to the second conveying device 5 at speed V2 at the time t=t2 with the revolving angle θ=θ1 (=π). Then, the end-effector 71 returns to an initial revolving position at the time t=t3 (=t1+T2) with the revolving angle of 2π.

Time zones a1, a3 and a5 synchronize with the conveying motion of the first conveying device 3 or the conveying motion of the second conveying device 5 for receipt or transfer of the transferring-work 2. In these time zones, the speed is maintained substantially constant so that a relative speed to the conveying speed of the transferring-work 2 is substantially zero. On the other hand, in the time zones a2 and a4, the revolving speed of the end-effector 71 is increased or reduced.

Also in the time zones a2 and a4, the revolution position is adjusted besides the adjustment of the speed. As shown in FIG. 11, the revolution position adjustment is performed, for example, when the conveying speed of the second conveying device 5 varies. In order to maintain a constant conveying interval when the conveying speed of the second conveying device 5 varies, timing for transferring the transferring-work 2 from the transfer device 6 to the second conveying device 5 needs to be adjusted. Thus, in order to adjust the timing, control of the revolution positions of the end-effectors 71 to 76 is performed.

For example, if a need arises to transfer the transferring-work 2 earlier by time Δt, the speed of the end-effector 71 is increased to cause the curve in FIG. 11 to pass a point f1 instead of a point f. This allows the transferring-work 2 to be transferred with high accuracy to a predetermined position such that a substantially constant conveying interval of the second conveying device 5 can be maintained.

Next, control of the rotating mechanism and the advancing and retracting mechanism will be described. The control device processes image data obtained by imaging device 105 to recognize target transfer positions on the second conveying device 5. The control device also processes image data obtained by imaging device 106 to recognize the position and attitude in the direction of the revolution axis CL (see FIG. 4) of each transferring-work 2 held by each holding surface 70s of the transfer device 6.

The control device of the transfer apparatus 1 in the embodiment calculates the amount of advance and retraction control of the holding surface 70s from a position in the direction of the revolution axis CL among the target transfer positions, and the position of the transferring-work 2 in the direction of the revolution axis CL. The control device also calculates the amount of rotation control of the transferring-work 2 by the rotating mechanism based on the attitude of the transferring-work 2. Then, the control device controls the motor 705 based on the calculated amount of advance and retraction control, and controls the motor 704 based on the calculated amount of rotation control.

As described above, the transfer apparatus 1 in the embodiment independently controls the revolution of the end-effectors 71 to 76 to achieve transfer at high speed with high accuracy. In the transfer apparatus 1 in the embodiment, the rotating mechanism and the advancing and retracting mechanism are controlled as described above to allow the transferring-work 2 to be transferred with higher accuracy.

With the transfer apparatus 1 in the embodiment, the transferring-works 2 can be continuously conveyed and placed on the carrier works 21 without being stopped. This allows accurately produced RF-TAGs to be produced in a large amount at low costs. The transfer apparatus 1 in the embodiment can be used, for example, for transferring or mounting electronic components to IC card components, besides for producing the RF-TAG components. The RF-TAG IC itself may be the transferring-work 2. Further, the transfer apparatus 1 in the embodiment may be used as a production facility used for a production process of sanitary products such as disposable diapers or sanitary napkins.

The transfer apparatus 1 in the embodiment can be used in various converting machines, printers, labelers, semiconductor producing devices, or the like. For example, the transfer apparatus 1 can be used for a production process of disposable diapers, sanitary napkins, tampons, or face masks. Further, the transfer apparatus 1 can be used for labeling with seal labels as transferring-works 2 and various products such as sanitary products or food products such as snacks as carrier works 21. Further, the transfer apparatus 1 can be used for packaging products with various products such as sanitary products or food products such as snacks as transferring-works 2 and packaging films as carrier works 21.

Further, in the embodiment, the individual carrier works 21 are used, but a long sheet-like material before being cut into individual pieces may be used instead. In this case, marks indicating target transfer positions may be applied on a surface of the long sheet-like material for image recognition. In this case, the revolution of the end-effectors 71 to 76 is controlled based on the target transfer positions indicated by the marks, thereby allowing transferring-works 2 to be transferred to a continuous sheet-like carrier work 21 with high accuracy. In production of RF-TAGs, on a long sheet-like carrier work 21 having antenna patterns formed thereon, the antenna patterns may be used as marks for image recognition. Specifically, patterns on the surface of the carrier work 21 may be used as the marks.

Embodiment 2

Figure 12:
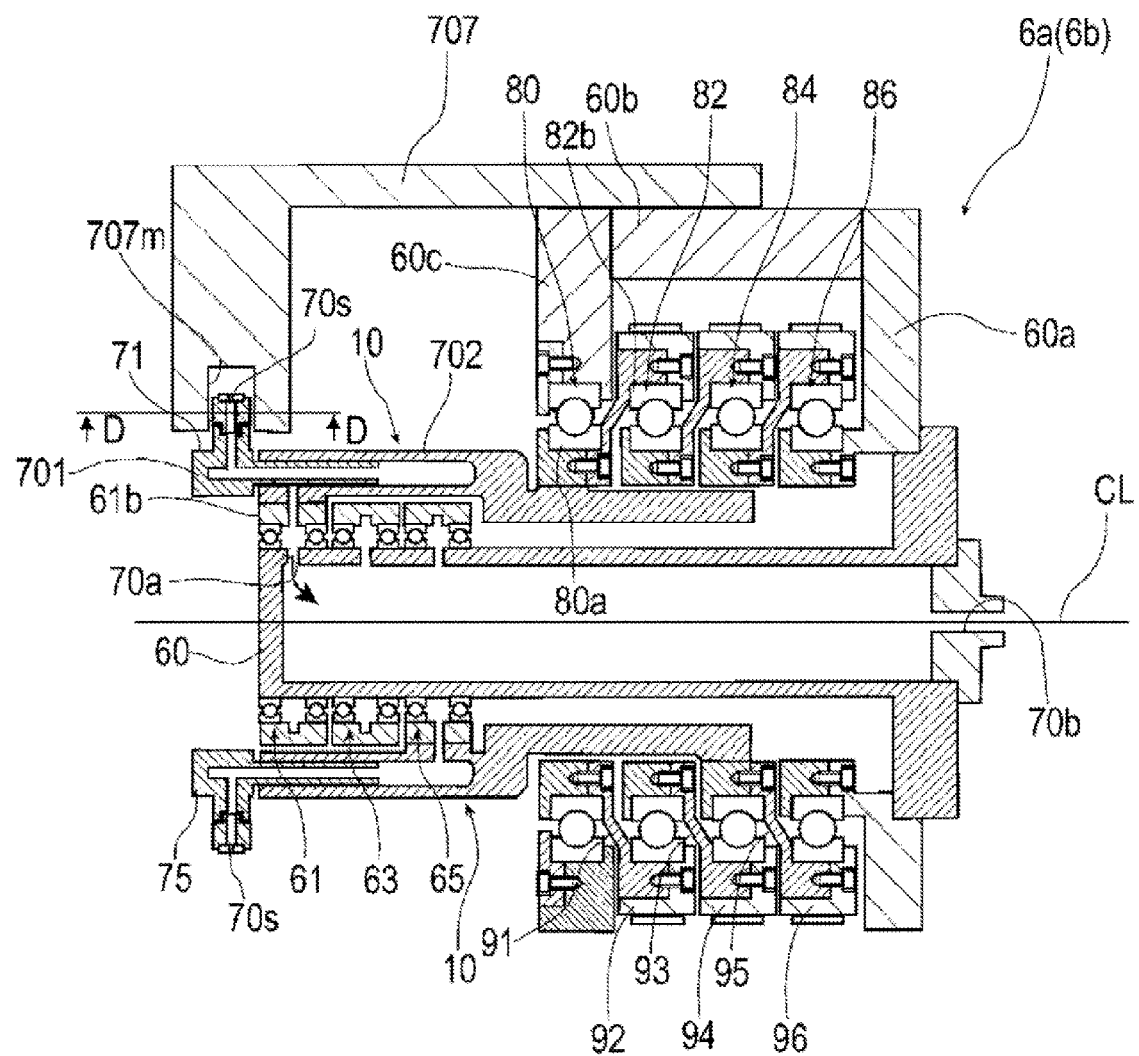
FIG. 12 is a block diagram of a sectional structure of a transfer device in Embodiment 2.

This embodiment is such that the configurations of the advancing and retracting mechanism and the rotating mechanism of the holding surface 70s are changed based on the transfer apparatus in Embodiment 1. This will be described with reference to FIGS. 12 and 13.

A transfer apparatus 1 in the second embodiment includes a guide member 707 for sliding a sliding member 701 of each of the end-effectors 71 to 76. The guide member 707 has a guide groove 707m that controls a position of a revolving holding base 703 in the direction of a revolution axis CL. The guide member 707 is held by a structure member 60b so as to be advanceable and retractable along the revolution axis CL. The guide member 707 operates so that the position of the holding base 703 of the end-effectors 71 to 76 in the direction of the revolution axis CL substantially matches a position of the guide groove 707m. In this embodiment, a motor provided in the structure member 60b controls the position of the guide member 707 in the direction of the revolution axis CL.

The guide member 707 is provided so that the guide groove 707m is positioned between revolution positions Q1 and Q4 (see FIG. 1) of the end-effectors 71 to 76. The guide groove 707m has a curved shape widely opening toward Q1 upstream in the revolution direction. In the transfer device 6 of the second embodiment, abutment between the curved shape and the holding base 703 causes the sliding member 701 to be advanced and retracted in the direction of the revolution axis CL, thereby changing the position of the holding base 703 in the direction of the revolution axis CL. This changes a position of a holding surface 70s in the direction of the revolution axis CL.

Figure 13:
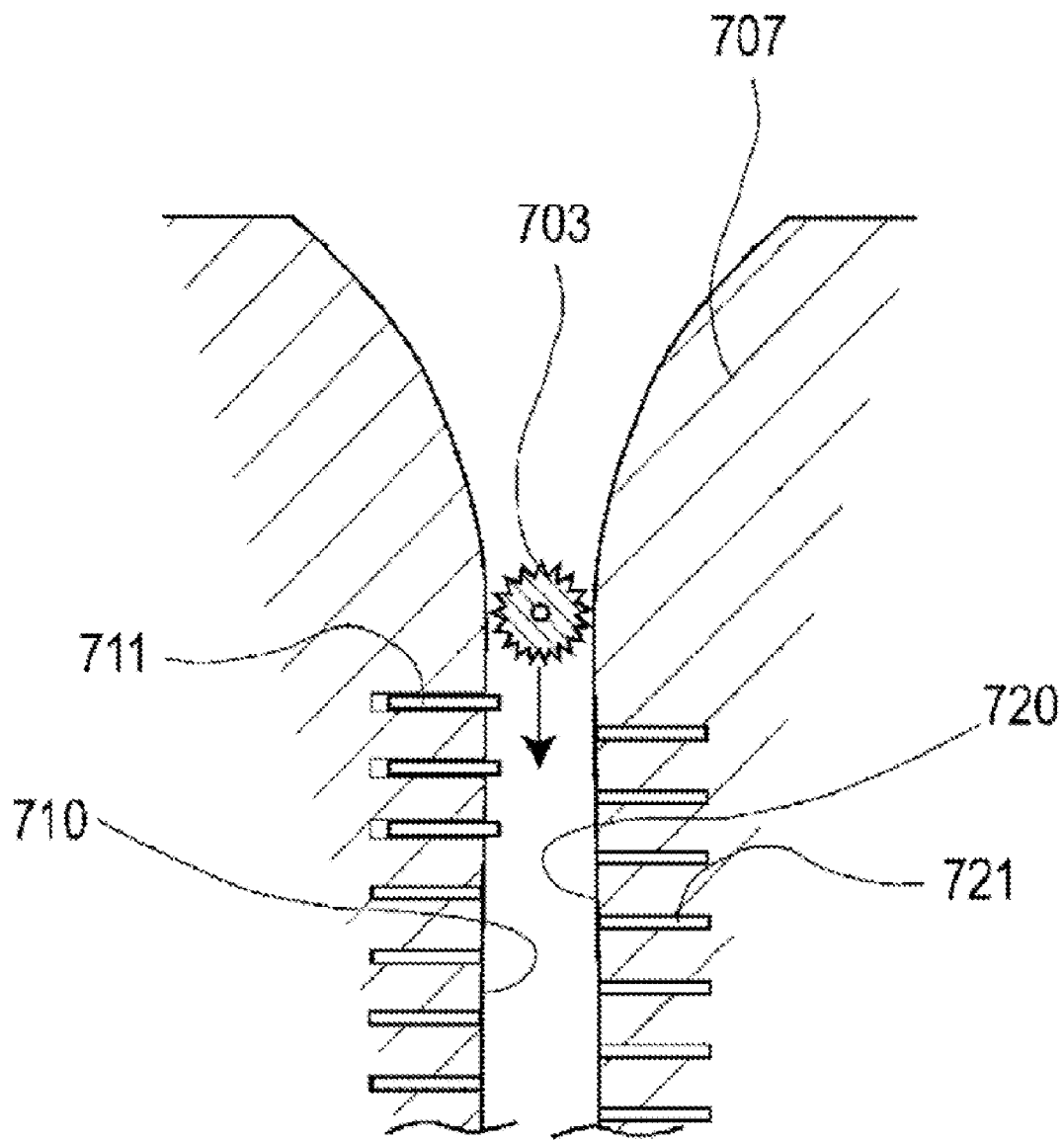
FIG. 13 is an enlarged sectional view of a guide groove in Embodiment 2, viewed along arrows D-D in FIG. 12.

As shown in FIG. 13, on inner peripheral surfaces 710 and 720 facing each other in the guide groove 707m protruding pins 711 and 721, which are independently pneumatically controlled, are placed so as to protrude toward the guide groove 707m. The holding base 703 in the second embodiment is rotatably supported by the sliding member 701 via a ratchet mechanism with a tooth angle of 0.5 degree.

Each protruding pin 711 protruding from the first inner surface 710 allows the holding base 703 rotatably supported via the ratchet mechanism to be rotated clockwise by one tooth. Each protruding pin 721 protruding from the second inner surface 720 allows the holding base 703 to be rotated counterclockwise by one tooth.

Specifically, in the rotating mechanism of the transfer device 6 in the second embodiment, the revolving position of the holding base 703 is controlled according to the number of the protruding pins 711 and 721 protruding from the inner surfaces 710 and 720. The revolving position of the holding base 703 is controlled to change the revolving position of the holding surface 70s.

Other configurations and the operation and effect are the same as in Embodiment 1. As a protruding mechanism of the protruding pins 711 and 721, various drive mechanisms such as a mechanism using hydraulic control or a mechanism using control with a solenoid (electromagnetic driving) may be used instead of the mechanism using the pneumatic control in the second embodiment.

Embodiment 3

Figure 14:
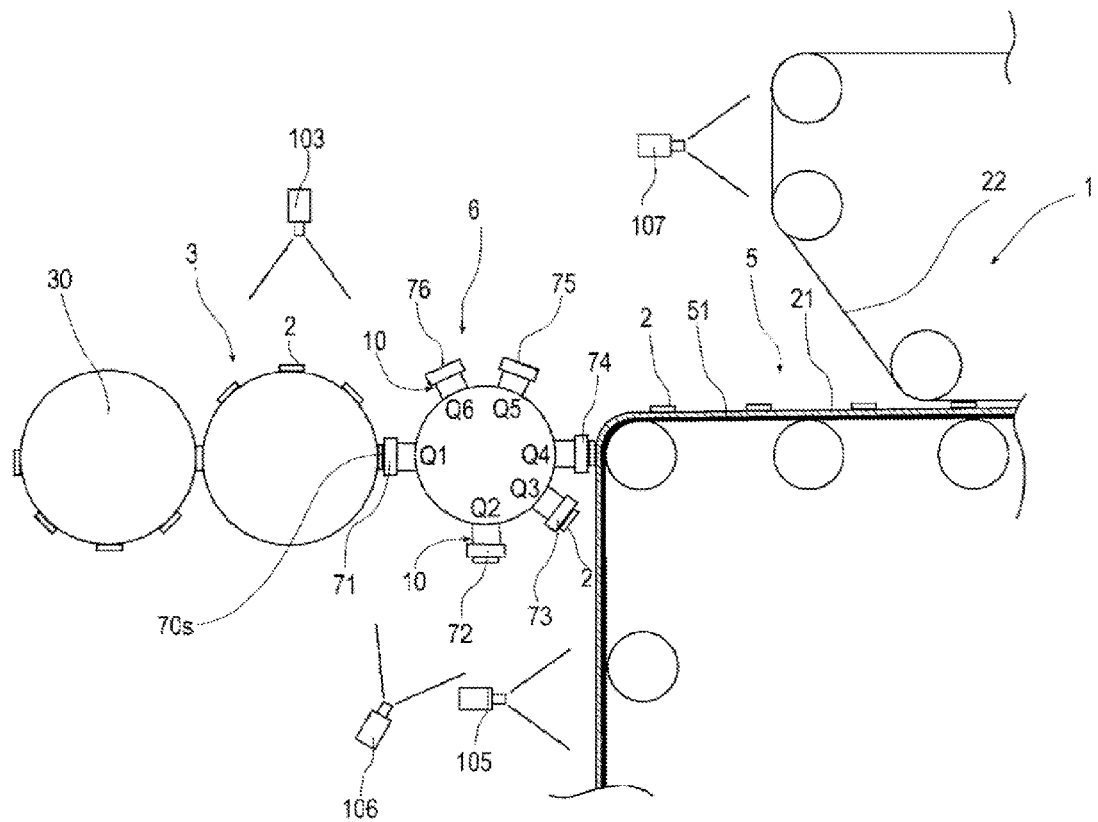
FIG. 14 is a block diagram of another transfer apparatus in Embodiment 3.

This embodiment is such that the carrier works 21 are changed into a continuous sheet material, and a mechanism for feeding a laminate film 22 is added, based on the transfer apparatus in Embodiment 1. This will be described with reference to FIG. 14.

In the third embodiment, the laminate film 22 is bonded to a surface of a carrier work 21 on which transferring-works 2 are placed. The laminate film 22 can provide an effect of protecting surfaces of products and increase weather resistance. Marks for alignment may be applied to the laminate film 22. In this case, an imaging device 107 is used to recognize the marks on the laminate film 22, thereby allowing the laminate film 22 to be aligned with the carrier work 21 with high accuracy. The imaging device 107 may include CCDs or CMOS devices, or inexpensive optical sensors.

Other configurations and the operation and effect are the same as in Embodiment 1.

Further, a continuous material (a continuous sheet material) of nonwoven fabric for substrates of disposable diapers may be used as a carrier work 21, and water-absorbing pads of pulp may be used as transferring-works 2 placed on the carrier work 21. In this case, printing a pattern on the laminate film 22 can enhance the design effect of the disposable diapers. Further, the laminate film 22 and the carrier work 21 may be aligned using the pattern. Specifically, the imaging device 107 recognizes the pattern on the laminate film 22 and detects a feeding position thereof, thereby achieving alignment between the laminate film 22 and the carrier work 21 with high accuracy.

Further, the transferring-works 2 may be snacks or the like, and the carrier work 21 and the laminate film 22 may be resin films such as polyethylene films. In this case, edges of the film-like carrier work 21 and laminate film 22 facing each other can be bonded to provide a bag-like package.

Having described hereinabove several embodiments as non-limiting examples in accordance with the present invention, it is to be understood that the present invention is not intended to be limited to the specific features recited in connection with the above-noted embodiments; but rather that diverse variants and modifications of the above-discussed embodiments, inter alia, are encompassed by the present invention, as relates to the accompanying claims and their equivalents.

The invention claimed is:

1. A transfer apparatus comprising:
    a first conveying device configured to hold and convey a transferring-work;
    a second conveying device configured to hold and convey a carrier work; and
    a transfer device configured to receive the transferring-work from the first conveying device and transfer the transferring-work to the carrier work,
    wherein the transfer device comprises two or more end-effectors that revolve along the same circumference to convey the transferring-work, each end-effector being connected to an external motor whose rotation is independently controlled,
    wherein each of the end-effectors is configured to revolve independently of at least any of the other end-effectors, and
    wherein each of the end-effectors has a holding surface configured to hold the transferring-work, and is configured to be able to advance and retract the holding surface along a revolution axis of the each end-effector.

2. The transfer apparatus according to claim 1, wherein the holding surface is configured to be rotatable around a central axis in the direction of the normal thereto.

3. The transfer apparatus according to claim 1, wherein the transfer apparatus comprises control means for controlling a revolution speed and a revolution position in revolution of the each end-effector, and
    wherein the control means is configured to perform control so that the revolution speed of the end-effector when receiving the work from the first conveying device substantially matches a conveying speed of the first conveying device, and a revolution speed of the end-effector when transferring the work to the second conveying device substantially matches a conveying speed of the second conveying device.

4. The transfer apparatus according to claim 1, wherein the transfer device includes coaxial rotors that integrally hold one or more end-effectors revolving therewith, and three or more bearings placed coaxially so as to rotatably support at least two coaxial rotors, each of the bearings includes a substantially cylindrical inner ring, a substantially cylindrical outer ring fitted from outside to the inner ring, and a bearing mechanism that allows relative rotation between the inner ring and the outer ring, wherein the inner ring of one or more middle bearings placed in an axially middle position among the bearings is connected to the outer ring of an adjacent bearing and is configured to integrally rotate therewith, and integrally holds any of the coaxial rotors, wherein the inner ring of one of bearings placed at axial ends among the bearings is connected to the outer ring of an adjacent bearing and is configured to integrally rotate therewith, and integrally holds any of the coaxial rotors, and the outer ring thereof is secured to a structure member of the transfer device, wherein the outer ring of the other of the bearings placed at the axial ends among the bearings is connected to the inner ring of an adjacent bearing and is configured to integrally rotate therewith, and the inner ring thereof is secured to a structure member of the transfer device, and the outer rings integrally connected to the inner rings of the adjacent bearings among the outer rings are connected to an output shaft of the external motor.

5. The transfer apparatus according to claim 1, further comprising a first measuring portion configured to detect a conveying position and a conveying speed of the transferring-work conveyed by the first conveying device.

6. The transfer apparatus according to claim 5, further comprising a second measuring portion configured to detect a target transfer position on a surface of the carrier work in the second conveying device and a movement speed thereof.

7. The transfer apparatus according to claim 6, further comprising a third measuring portion configured to detect an attitude and a position of the transferring-work held by the holding surface of the end-effector.

8. The transfer apparatus according to claim 1, wherein the first and the second conveying devices each include a roller or a translating conveyor belt, and are configured to convey the transferring-work or the carrier work placed on a surface of the roller or the conveyer belt.

9. The transfer apparatus according to claim 1, wherein the transferring-work is an interposer on which IC chips for RF-TAGs are mounted and an enlarged electrode electrically extended from electrodes of the IC chips is formed, and the carrier work is an antenna sheet having an antenna pattern for radio communication formed on a sheet substrate.

10. A transfer apparatus comprising:
a first conveying device configured to hold and convey a transferring-work;
a second conveying device configured to hold and convey a carrier work; and
a transfer device configured to receive the transferring-work from the first conveying device and transfer the transferring-work to the carrier work,
wherein the transfer device comprises two or more end-effectors that revolve along the same circumference to convey the transferring-work, each end-effector being connected to an external motor whose rotation is independently controlled,
wherein each of the end-effectors is configured to revolve independently of at least any of the other end-effectors, and
wherein each of the end-effectors has a holding surface configured to hold the transferring-work, and the holding surface is configured to be rotatable around a central axis in the direction of the normal thereto.

11. The transfer apparatus according to claim 10, wherein the transfer apparatus comprises control means for controlling a revolution speed and a revolution position in revolution of the each end-effector, and wherein the control means is configured to perform control so that a revolution speed of the end-effector when receiving the work from the first conveying device substantially matches a conveying speed of the first conveying device, and a revolution speed of the end-effector when transferring the work to the second conveying device substantially matches a conveying speed of the second conveying device.

12. The transfer apparatus according to claim 10, wherein the transfer device includes coaxial rotors that integrally hold one or more end-effectors revolving therewith, and three or more bearings placed coaxially so as to rotatably support at least two coaxial rotors, wherein each of the bearings includes a substantially cylindrical inner ring, a substantially cylindrical outer ring fitted from outside to the inner ring, and a bearing mechanism that allows relative rotation between the inner ring and the outer ring, wherein the inner ring of one or more middle bearings placed in an axially middle position among the bearings is connected to the outer ring of adjacent another bearing and is configured to integrally rotate therewith, and integrally holds any of the coaxial rotors, wherein the inner ring of one of bearings placed at axial ends among the bearings is connected to the outer ring of adjacent another bearing and is configured to integrally rotate therewith, and integrally holds any of the coaxial rotors, and the outer ring thereof is secured to a structure member of the transfer device, wherein the outer ring of the other of the bearings placed at the axial ends among the bearings is connected to the inner ring of adjacent another bearing and is configured to integrally rotate therewith, and the inner ring thereof is secured to a structure member of the transfer device, and wherein the outer rings integrally connected to the inner rings of the adjacent bearings among the outer rings are connected to an output shaft of the external motor.

13. The transfer apparatus according to claim 10, further comprising a first measuring portion configured to detect a conveying position and a conveying speed of the transferring-work conveyed by the first conveying device.

14. The transfer apparatus according to claim 13, further comprising a second measuring portion configured to detect a target transfer position on a surface of the carrier work in the second conveying device and a movement speed thereof.

15. The transfer apparatus according to claim 14, further comprising a third measuring portion configured to detect an attitude and a position of the transferring-work held by the holding surface of the end-effector.

16. The transfer apparatus according to claim 10, wherein the first and the second conveying device each include a roller or a translating conveyor belt, and are configured to convey the transferring-work or the carrier work placed on a surface of the roller or the conveyer belt.

17. The transfer apparatus according to claim 10, wherein the transferring-work is an interposer on which IC chips for RF-TAGs are mounted and an enlarged electrode electrically extended from electrodes of the IC chips is formed, and the carrier work is an antenna sheet having an antenna pattern for radio communication formed on a sheet substrate.

* * * * *